(12) United States Patent
Zowtiak et al.

(10) Patent No.: US 6,189,534 B1
(45) Date of Patent: Feb. 20, 2001

(54) BI-FUNCTIONAL IN-LINE PHONATION VALVE

(75) Inventors: John Zowtiak, Coto De Caza; John O'Mahony, Carlsbad; David Frigger, Lake Forest, all of CA (US)

(73) Assignee: Mallinckrodt Inc., St. Louis, MO (US)

( * ) Notice: Under 35 U.S.C. 154(b), the term of this patent shall be extended for 0 days.

(21) Appl. No.: 09/170,037

(22) Filed: Oct. 13, 1998

(51) Int. Cl.[7] ................................................ A61M 16/00
(52) U.S. Cl. ................................. 128/207.16; 128/207.14
(58) Field of Search ........................... 606/1; 128/200.24, 128/201.28, 204.18, 207.14, 207.16, 207.29, 201.19, 205.24

(56) References Cited

U.S. PATENT DOCUMENTS

| | | |
|---|---|---|
| 3,137,299 | 6/1964 | Tabor . |
| 3,827,440 | 8/1974 | Birch et al. . |
| 3,924,637 | 12/1975 | Swanson . |
| 3,990,439 | 11/1976 | Klinger . |
| 4,040,428 | 8/1977 | Clifford . |
| 4,325,366 | 4/1982 | Tabor . |
| 4,538,607 | 9/1985 | Saul . |
| 4,627,433 | 12/1986 | Lieberman . |
| 4,759,356 | 7/1988 | Muir . |
| 4,971,054 | 11/1990 | Andersson et al. . |
| 5,107,828 | 4/1992 | Koss et al. . |
| 5,259,378 | 11/1993 | Huchon et al. . |
| 5,626,132 * | 5/1997 | Miller et al. ............... 128/207.16 |
| 5,765,560 | 6/1998 | Verkerke et al. . |
| 5,806,515 * | 9/1998 | Bare et al. ................. 128/207.16 |
| 5,813,402 * | 9/1998 | Jinotti ........................ 128/207.16 |
| 6,030,350 * | 2/2000 | Jiang et al. ..................... 600/587 |

FOREIGN PATENT DOCUMENTS

| | | |
|---|---|---|
| 85 14 859 | 7/1985 | (DE) . |
| 0385250 | 9/1990 | (EP) . |
| 2164424 | 3/1986 | (GB) . |

\* cited by examiner

*Primary Examiner*—Glenn K. Dawson
(74) *Attorney, Agent, or Firm*—Rothwell, Figg, Ernst & Manbeck, P.C.

(57) ABSTRACT

An in-line phonation valve system including a valve body having first and second ends through which gas passes into and out of the valve body. The first end is connectable to a breathing tube connected to a patient's airway, for passage of gas between the breathing tube and the valve body. The second end of the valve body is connectable to a gas line. A diaphragm-valve assembly is provided which includes a one-way valve having a phonation position permitting gas to pass through said valve body toward said patient when said patient inhales. The one-way valve in the phonation position substantially prevents gas from passing through the valve body when the patient exhales. The diaphragm-valve assembly is movable out of the phonation position, so as to permit substantially free flow of gas through the valve body both toward and away from the patient when the patient respectively inhales and exhales. The diaphragm-valve assembly is movable from the phonation position without disconnecting the first end from the breathing tube and the second end from the gas line. Preferably, the diaphragm-valve assembly is a removable cartridge which is replaceable with a free-flowing ring cartridge insert.

3 Claims, 4 Drawing Sheets

BI-FUNCTIONAL IN-LINE PHONATION VALVE

BACKGROUND OF THE INVENTION

1. Field of the Invention

The present invention relates to an in-line phonation valve for a breathing tube such as a tracheostomy tube.

2. Description of the Background Art

Phonation valves permit speaking by a patient having a breathing tube inserted into the patient's airway, such as a tracheostomy tube inserted into a patient's trachea.

Various valves for tracheostomy tubes are known in the art, including those disclosed in U.S. Pat. Nos. 3,137,299, 4,040,428, 4,325,366, 4,759,356, 4,971,054 and 5,259,378. Also of interest are U.S. Pat. Nos. 3,924,637, 3,990,439, 4,538,607 and 4,627,433.

In-line phonation valves have one end connected to a breathing tube inserted into a patient's body. A second end of an in-line phonation valve is connected to a gas line of a ventilator circuit.

Prior in-line phonation valves are unidirectional (one-way) valves that allow inspiration only. This results in expiration through the patient's voice box allowing the patient to speak.

Typically, phonation valves are used only temporarily for speaking, and the ventilator circuits must be disconnected for removing the phonation valves. Additionally, in-line phonation valves must frequently be cleaned.

There remains a need in the art for improved in-line phonation valves.

SUMMARY OF THE INVENTION

In accordance with the present invention, an in-line phonation valve system comprises a valve body having first and second ends through which gas passes into and out of the valve body. The first end is connectable to a breathing tube connected to a patient's airway, for passage of gas between the breathing tube and the valve body. The second end of the valve body is connectable to a gas line. A diaphragm-valve assembly is provided which comprises a one-way valve having a phonation position permitting gas to pass through said valve body toward said patient when said patient inhales. The one-way valve in the phonation position substantially prevents gas from passing through the valve body when the patient exhales. The diaphragm-valve assembly is movable out of the phonation position, so as to permit substantially free flow of gas through the valve body both toward and away from the patient when the patient respectively inhales and exhales. The diaphragm-valve assembly is movable from the phonation position without disconnecting the first end from the breathing tube and the second end from the gas line.

DETAILED DESCRIPTION OF THE PREFERRED EMBODIMENTS

FIGS. 1A–1D show an in-line phonation valve 10 in accordance with one embodiment of the present invention. Phonation valve 10 includes a valve body 12 having first and second ends 14 and 16 respectively through which gas, such as air, oxygen or anesthesia gas, passes into and out of valve 10.

Figure 2:
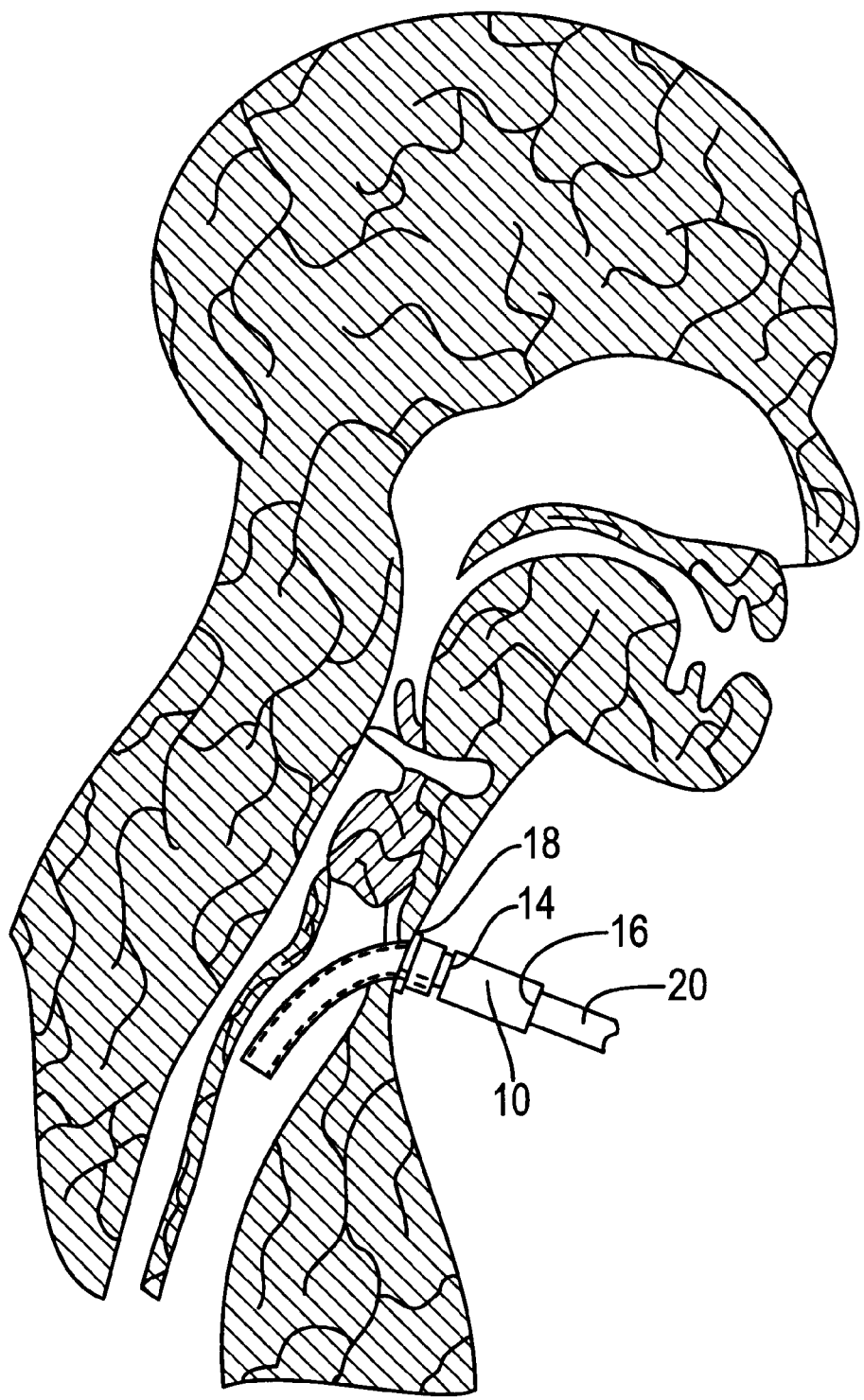
FIG. 2 is a schematic illustration, partially in cross-section, showing use of a phonation valve in accordance with the present invention.

The first end 14 of valve 10 is connectable to a breathing tube such as tracheostomy tube 18 shown in FIG. 2. Phonation valve 10 is an in-line phonation valve wherein the second end 16 is connectable to a source of gas such as oxygen (not shown) by line 20 of, for example, a ventilator circuit.

Referring back to FIGS. 1A–1D, a valve seat 22 is located within the valve body 12 between the first and second ends 14 and 16 respectively. A thin, flexible diaphragm 24 is mounted circumferentially around a stem 26, and can be held on to stem 26 by any suitable means such as a mechanical fit. A diaphragm 24 can be formed of any suitable thin, flexible material, such as silicone rubber, and can have any suitable thickness, such as about 0.0050–0.02 inch.

Figure 1A:
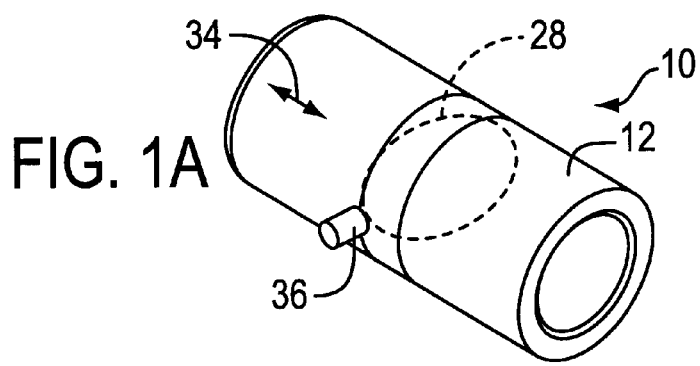
FIG. 1A is a perspective view of a phonation valve in accordance with one embodiment of the present invention.
Figure 1B:
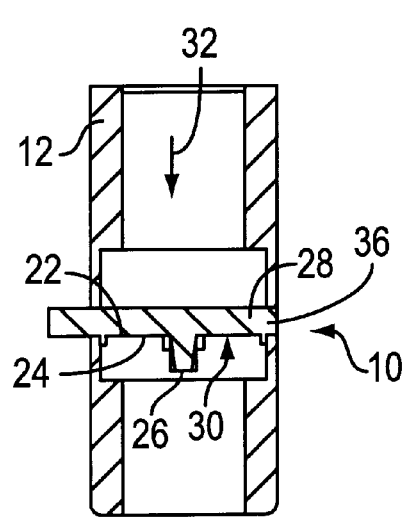
FIG. 1B is a partly schematic cross-sectional view of the valve of FIG. 1 in a phonation position.

In the embodiment shown in FIGS. 1A–1D, a diaphragm-valve assembly 28 is shown. Diaphragm-valve assembly 28 is comprised of a one-way valve 30 having a phonation position as shown in FIG. 1B which permits gas to pass through valve body 12 toward a patient in the direction shown by arrow 32 when the patient inhales. One-way valve 30, when in the phonation position shown in FIG. 1B, substantially prevents gas from passing through valve body 12 when the patient exhales.

The diaphragm-valve assembly 28 is movable from the phonation position shown in FIG. 1B to the position shown in phantom lines in FIG. 1A, so as to permit substantially free flow of gas through valve body 10 both toward and away from the patient when the patient respectively inhales and exhales, in the directions of double-headed arrow 34.

Figure 1C:
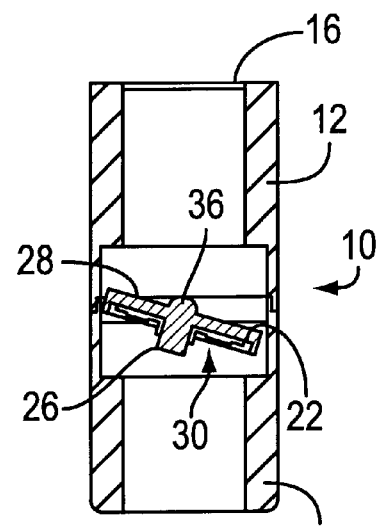
FIG. 1C is a partly schematic cross-section of the valve of FIG. 1A in an intermediate position.

In the embodiment shown in FIGS. 1A–1D, the diaphragm-valve assembly 28 includes a pivot 36 connecting the valve assembly 28 to valve body 12, for rotating the valve assembly 28 within valve body 12 from the phonation position shown in FIG. 1B, through the intermediate position shown in FIG. 1C to the free-flow position shown in FIG. 1A, wherein the valve assembly 28 is positioned longitudinally within the valve body 12 so as to permit substantially free flow of gas.

As can be seen, the diaphragm-valve assembly is movable from the phonation position, without the need to disconnect the first and second ends 14 and 16 of the valve body from any tubes or lines.

Figure 1D:
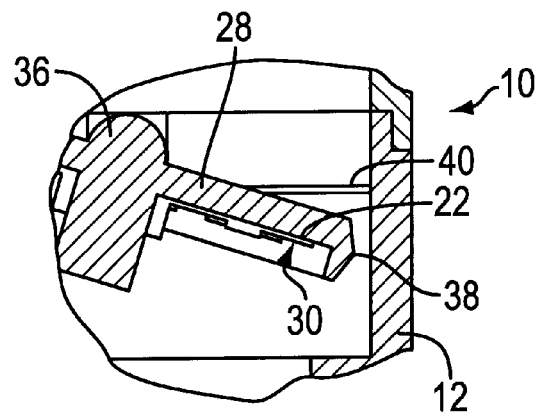
FIG. 1D is a partly schematic cross-sectional detail of FIG. 1C.

As shown in FIG. 1D, valve assembly 28 has a peripheral edge 38 that seats within an inner wall detent 40 of the valve body 12 when the valve assembly is in the phonation position shown in FIG. 1B.

Figure 3A:
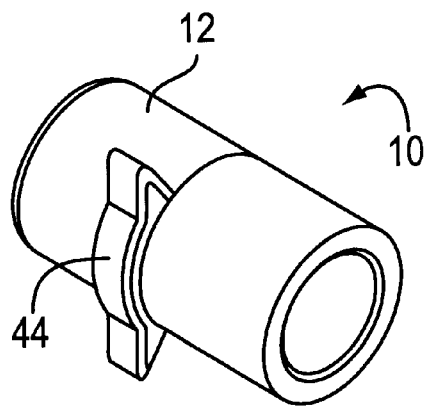
FIG. 3A is a perspective view of a second embodiment of the present invention.
Figure 3B:
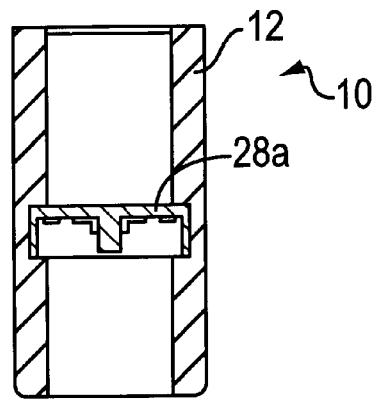
FIG. 3B is a partly schematic cross-section of the valve of FIG. 3A, in a phonation position.
Figure 3C:
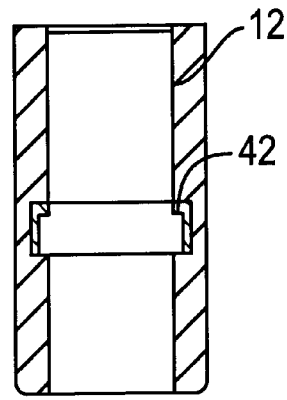
FIG. 3C is a partly schematic cross-section of the valve of FIG. 3A in a free-flow configuration.

A second embodiment is shown in FIGS. 3A–3C. According to this embodiment, a valve assembly 28a shown in FIG. 3B is completely removable from the valve body 12, and replaceable with an open, valve body ring cartridge insert 42 shown in FIG. 3C, so as to permit substantially free flow of gas through valve body 12. Both valve assembly 28a and ring insert 42 include finger tabs 44, shown in FIG. 3A, for removal and insertion into valve body 12.

Figure 4A:
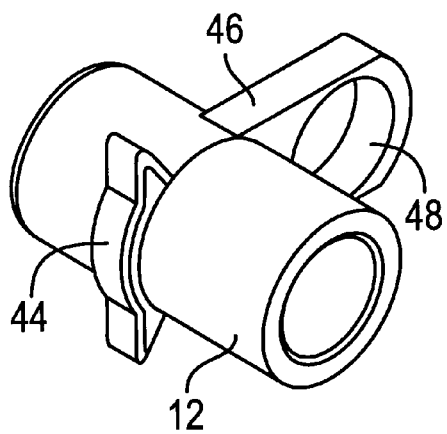
FIG. 4A is a perspective view of a third embodiment of the present invention.
Figure 4B:
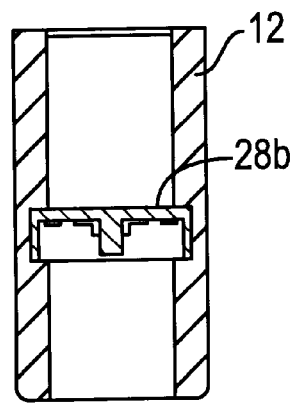
FIG. 4B is a partly schematic cross-section of the valve of FIG. 4A, in a phonation position.
Figure 4C:
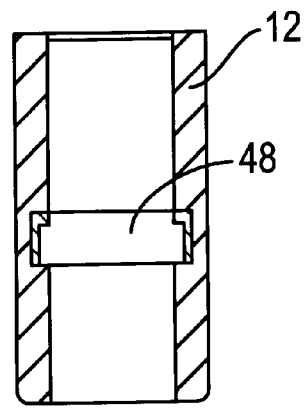
FIG. 4C is a partly schematic cross-section of the valve of FIG. 4A in a free-flow configuration.

FIGS. 4A–4C show a third embodiment in accordance with the present invention. According to this embodiment, the diaphragm-valve assembly 28b, shown clearly in FIG. 4B, is positioned within a laterally slidable member 46 within the valve body 12, as shown in FIG. 4A. The slidable member 46 includes a two-way gas passageway 48 therein.

The slidable member 46 is slidable from the phonation position shown in FIG. 4B, wherein the diaphragm-valve assembly 28b is positioned within the valve body 12, to a position wherein the two-way gas passageway 48 is positioned within valve body 12 as shown in FIG. 4C so as to permit substantially free flow of gas through valve body 12.

The slidable member 46 is provided with finger tabs 44a for sliding the valve between the position shown in FIG. 4B and FIG. 4C.

The present invention permits switching of an in-line phonation valve from a unidirectional phonation position allowing a patient to speak, to a bi-directional ventilation position, without disconnecting the phonation valve from ventilator circuitry.

What is claimed is:

1. An in-line phonation valve system, comprising:

a valve body having first and second ends through which gas passes into and out of the valve body, the first end connectable to a breathing tube connected to a patient's airway for passage of gas between said breathing tube and said valve body, the second end connectable to a gas line, a diaphragm-valve assembly comprising a one-way valve having a phonation position permitting gas to pass through said valve body toward said patient when said patient inhales, said one-way valve in said phonation position substantially preventing gas from passing through said valve body when said patient exhales, said diaphragm-valve assembly being moveable from said phonation position so as to permit substantially free flow of gas through said valve body both toward and away from said patient when said patient respectively inhales and exhales, wherein said diaphragm-valve assembly is moveable out of said phonation position without disconnecting said first end from said breathing tube or said second end from said gas line, so as to permit said substantially free flow of gas, wherein said diaphragm-valve assembly includes a pivot connecting said valve assembly to said valve body, for rotating said valve assembly within said valve body from said phonation position, to a free-flow position wherein said valve assembly is positioned longitudinally within said valve body, so as to permit said substantially free flow of gas.

2. The phonation valve system of claim 1 wherein said valve assembly has a peripheral edge which seats within an inner wall detent of said valve body when said valve assembly is in said phonation position.

3. An in-line phonation valve system, comprising:

a valve body having first and second ends through which gas passes into and out of the valve body, the first end connectable to a breathing tube connected to a patient's airway for passage of gas between said breathing tube and said valve body, the second end connectable to a gas line, a diaphragm-valve assembly comprising a one-way valve having a phonation position permitting gas to pass through said valve body toward said patient when said patient inhales, said one-way valve in said phonation position substantially preventing gas from passing through said valve body when said patient exhales, said diaphragm-valve assembly being moveable from said phonation position so as to permit substantially free flow of gas through said valve body both toward and away from said patient when said patient respectively inhales and exhales, wherein said diaphragm-valve assembly is moveable out of said phonation position without disconnecting said first end from said breathing tube or said second end from said gas line, so as to permit said substantially free flow of gas, wherein said diaphragm-valve assembly is positioned within a laterally slidable member within said valve body, wherein said slidable member includes a two-way gas passageway therein, and wherein said slidable member is slidable from said phonation position in which said diaphragm-valve assembly is positioned within said valve body, to a position wherein said two-way gas passageway is positioned within said valve body to permit said substantially free flow of gas.

* * * * *